US011224357B2

(12) United States Patent
Ikeda et al.

(10) Patent No.: US 11,224,357 B2
(45) Date of Patent: Jan. 18, 2022

(54) LIVING BODY INFORMATION IDENTIFICATION SYSTEM AND METHOD

(71) Applicant: Panasonic Corporation, Osaka (JP)

(72) Inventors: Takuma Ikeda, Osaka (JP); Hiroyuki Tani, Hyogo (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 16/792,604

(22) Filed: Feb. 17, 2020

(65) Prior Publication Data

US 2020/0297242 A1 Sep. 24, 2020

(30) Foreign Application Priority Data

Mar. 18, 2019 (JP) .............................. JP2019-049606

(51) Int. Cl.
| | |
|---|---|
| *G08B 1/08* | (2006.01) |
| *A61B 5/11* | (2006.01) |
| *H04W 4/029* | (2018.01) |
| *G01S 13/76* | (2006.01) |
| *A61B 5/00* | (2006.01) |

(52) U.S. Cl.
CPC ................ *A61B 5/11* (2013.01); *A61B 5/68* (2013.01); *G01S 13/765* (2013.01); *H04W 4/029* (2018.02)

(58) Field of Classification Search
CPC . A61B 5/11; A61B 5/68; H04W 4/029; G01S 13/765
USPC ..................................................... 340/539.1
See application file for complete search history.

(56) References Cited

U.S. PATENT DOCUMENTS

| | | | |
|---|---|---|---|
| 6,775,323 B1* | 8/2004 | Vasudevan Pillai .. | G01S 13/751 340/10.4 |
| 8,095,177 B2 | 1/2012 | Ida | |
| 10,445,539 B2* | 10/2019 | Hattori ............... | G06K 19/0723 |
| 10,477,355 B1* | 11/2019 | Niranjayan ....... | E04F 15/02405 |
| 2006/0013070 A1* | 1/2006 | Holm ....................... | G01S 5/18 367/128 |

(Continued)

FOREIGN PATENT DOCUMENTS

| | | |
|---|---|---|
| JP | 2001-183455 | 7/2001 |
| JP | 2002-058648 | 2/2002 |

(Continued)

*Primary Examiner* — Zhen Y Wu

(74) *Attorney, Agent, or Firm* — Wenderoth, Lind & Ponack L.L.P.

(57) ABSTRACT

Provided is a living body information identification system that can identify position information of a living body (a person) and state information about a state of the living body without attaching a wireless device or a sensor on a human body. The living body information identification system includes a transceiver configured to transmit radio waves and wirelessly receive a signal, and sensor modules configured to receive the radio waves, convert the received radio waves into power, and use the power as a power supply to transmit own unique ID information to the transceiver. The sensor modules receive the radio waves from the transceiver, convert the received radio waves into power, and use the power as a power supply to transmit state information about a state of the living body to the transceiver. The transceiver identifies the living body based on the ID information and the state information.

17 Claims, 3 Drawing Sheets

(56) References Cited

U.S. PATENT DOCUMENTS

| | | | | |
|---|---|---|---|---|
| 2007/0159332 | A1* | 7/2007 | Koblasz | G08B 21/0275 340/572.1 |
| 2008/0238682 | A1* | 10/2008 | Kuwako | H01Q 1/2216 340/572.4 |
| 2009/0184802 | A1* | 7/2009 | Park | G06K 17/0029 340/10.1 |
| 2010/0291879 | A1* | 11/2010 | Konishi | G01S 5/0252 455/67.11 |
| 2011/0080264 | A1* | 4/2011 | Clare | G01S 13/82 340/10.1 |
| 2012/0133490 | A1* | 5/2012 | Downie | G06K 19/0717 340/10.1 |
| 2014/0015642 | A1* | 1/2014 | White | G06K 7/10188 340/10.1 |
| 2015/0222370 | A1* | 8/2015 | Shinotsuka | G01S 5/18 367/137 |
| 2015/0379860 | A1* | 12/2015 | Vardi | G08B 21/0275 340/8.1 |
| 2016/0217664 | A1* | 7/2016 | Bradford | E04F 15/02 |
| 2016/0240052 | A1* | 8/2016 | Hyde | G08B 7/066 |
| 2016/0249160 | A1* | 8/2016 | Shinotsuka | G01S 1/75 |
| 2017/0116445 | A1* | 4/2017 | Debates | G06K 19/07345 |
| 2017/0287313 | A1* | 10/2017 | Park | A61B 5/00 |
| 2017/0354350 | A1* | 12/2017 | Di Croce | A61B 5/1117 |
| 2018/0003847 | A1* | 1/2018 | Casimiro | G01V 3/088 |
| 2018/0089475 | A1* | 3/2018 | Hattori | G06K 19/0723 |
| 2019/0126779 | A1 | 5/2019 | Saitou et al. | |
| 2019/0239813 | A1* | 8/2019 | Sai | A61B 5/0002 |
| 2019/0333354 | A1* | 10/2019 | Schwab | G08B 25/009 |
| 2021/0106256 | A1* | 4/2021 | Kogure | A61B 5/4561 |

FOREIGN PATENT DOCUMENTS

| | | |
|---|---|---|
| JP | 2004-271372 | 9/2004 |
| JP | 2009-268016 | 11/2009 |
| JP | 2018-004369 | 1/2018 |

* cited by examiner

LIVING BODY INFORMATION IDENTIFICATION SYSTEM AND METHOD

TECHNICAL FIELD

The technical field relates to a living body information identification system that identifies information of a living body.

BACKGROUND

In recent years, attention has been paid to efforts to collect a position of a person and information of a living body and use the position of a person and the information of a living body for monitoring and health management with an advancement of IoT. For example, JP-A-2001-183455 (Patent Literature 1) proposes a moving body position measuring system using RFID tags that can communicate with each other at a short indoor distance in order to detect a position of a person.

The moving body position measuring system disclosed in Patent Literature 1 describes the following matters. A plurality of ID tags having unique ID information are provided on a floor. When a person moves on the floor, an ID reader attached to the person reads information of an adjacent ID tag. The presence of a human body at a position of the ID tag whose ID tag information is read can be measured, and further a direction of a moving body can be measured based on a vector direction.

However, the human body position measuring system in the related art measures a position using the ID reader. Although the ID reader can measure a position of the human body, the ID reader cannot acquire a state about the human body. In addition, it is necessary to replace or periodically charge a battery in order to drive the battery.

SUMMARY

An object of the present disclosure is to provide a living body information identification system that identifies a position of a living body and state information about a state of the living body by using a small terminal that does not need to charge or replace a battery.

The living body information identification system according to the present disclosure identifies information of the living body. The living body information identification system includes a transceiver configured to transmit radio waves and wirelessly receive a signal, and sensor modules configured to receive the radio waves, convert the received radio waves into power, and use the power as a power supply to transmit own unique ID information to the transceiver. The sensor modules use the power as a power supply to acquire state information about a state of the living body and transmit the state information to the transceiver. The transceiver identifies the living body based on the ID information and the state information.

The living body information identification system according to the present disclosure can identify position information of a living body (a person) and state information about a state of the living body without attaching a wireless device or a sensor on a human body.

DESCRIPTION OF EMBODIMENTS

Hereinafter, embodiments of the present disclosure will be described with reference to the drawings.

<Structure>

Figure 1:
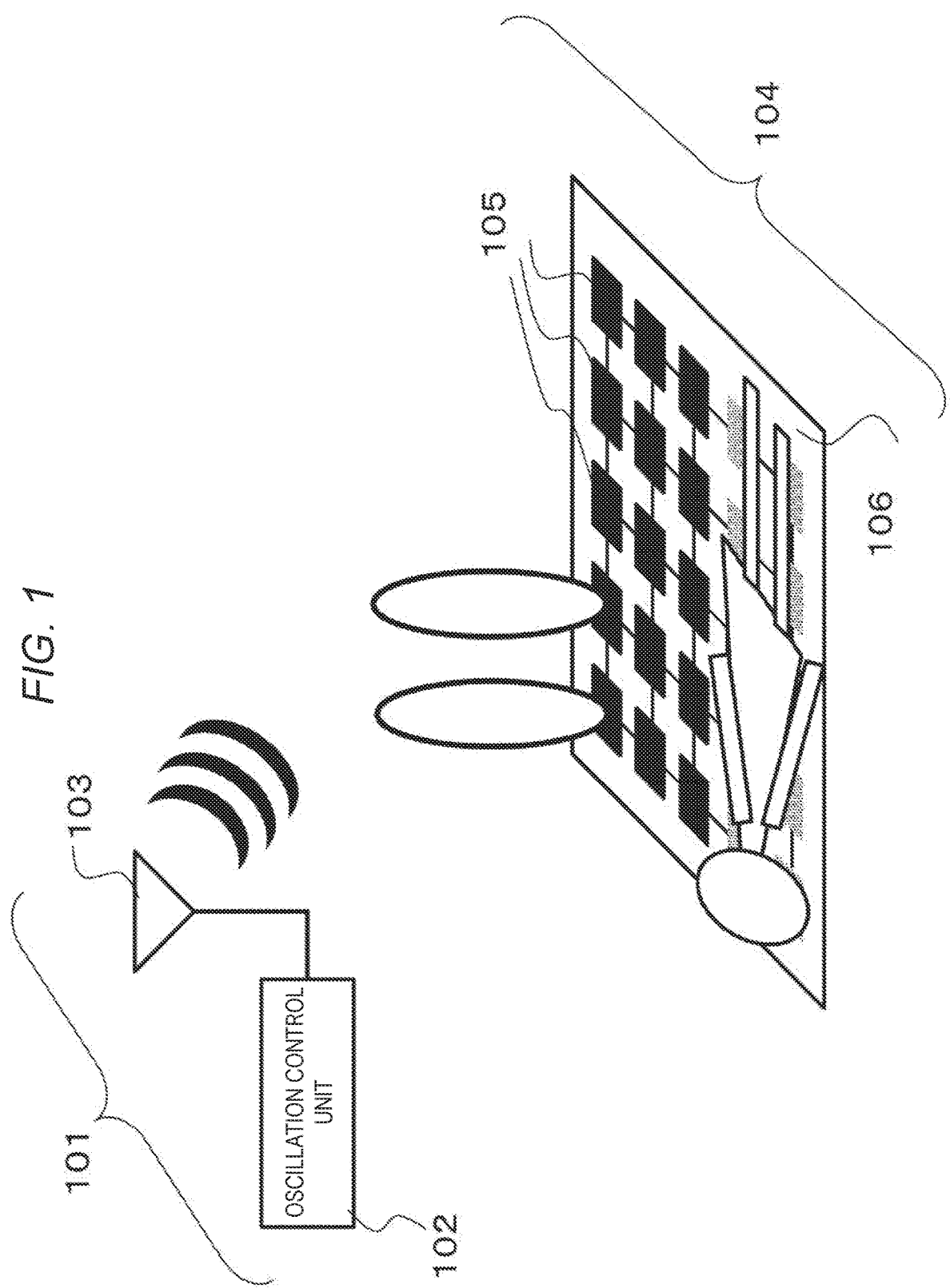
FIG. 1 shows an overall configuration of a living body information identification system according to an embodiment.

FIG. 1 is a perspective view showing an overall configuration of a living body information identification system according to the present embodiment. A living body in the present specification is a concept including a human body and an animal. Hereinafter, an example applied to a living body, especially a human body, will be described in the present embodiment.

<Configuration>

Figure 2:
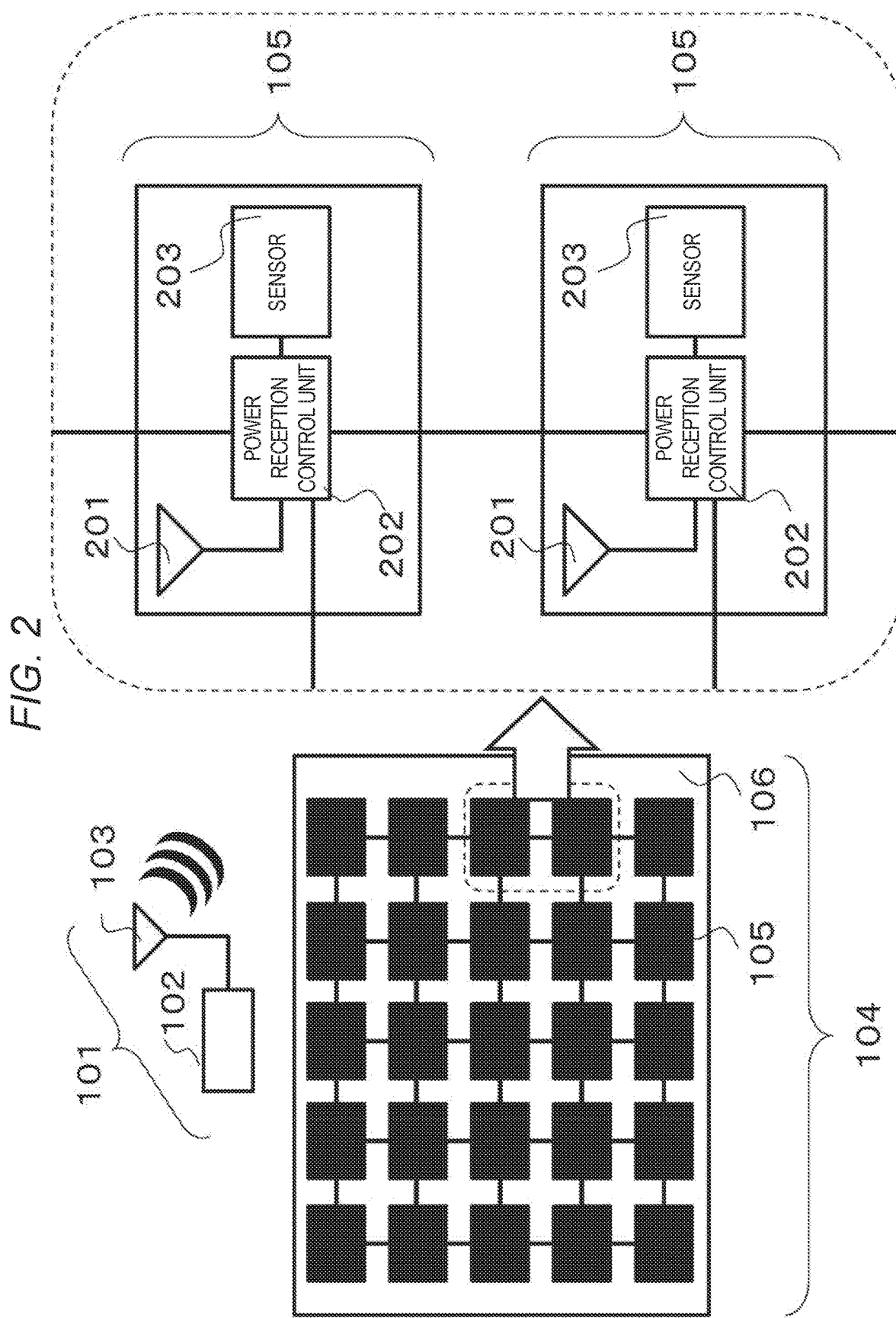
FIG. 2 shows in detail the living body information identification system and sensor modules according to the embodiment.

FIGS. 1 and 2 show the entire living body information identification system according to the present embodiment. A sensing device of a moving body includes a transceiver 101 and a sensor sheet 104. Next, each configuration will be described in detail.

<Transceiver 101>

The transceiver 101 includes an oscillation control unit 102 and a first antenna 103. The transceiver 101 has a function of generating high frequency power and transmitting the high frequency power as radio waves to space. The transceiver 101 has a function of instructing sensor modules 105 to transmit information and acquiring state information about a human body from the sensor modules 105.

<Oscillation Control Unit 102>

The oscillation control unit 102 has a function of generating high frequency power. The oscillation control unit 102 is implemented by an electrical circuit such as a crystal oscillator, a phase lock loop (PLL), and an amplifier circuit (AMP), and generates high frequency power. A frequency of the generated high frequency power is not particularly limited as long as the frequency of the generated high frequency power is in a microwave band such as a 900 MHz band, a 2.45 GHz band, and a 5.8 GHz band. The generated high frequency power is appropriately selected according to a power transmission distance and a size of the transceiver.

The oscillation control unit 102 controls transmission and reception of the generated high frequency power as radio waves, and acquires and stores information transmitted from the sensor modules 105 to be described later. The oscillation control unit 102 includes a functional device such as a memory, a CPU, and a communication device, and a functional device such as an electrical circuit.

<First Antenna 103>

The first antenna 103 has a function of transmitting the high frequency power generated by the oscillation control unit 102 as radio waves to space, and a function of acquiring radio waves transmitted to other devices (for example, the sensor modules 105 in the present embodiment) and radio waves transmitted from the other devices. The first antenna 103 is preferably a directional antenna or the like. The directional antenna has a planar shape, and is a patch antenna having a structure in which a dielectric substrate is interposed between a GND plate and an antenna plate.

<Position of Transceiver 101>

The transceiver 101 needs to be provided, for example, at a high position of four corners of a room in order to transmit high frequency power to the sensor modules 105 without leakage. If the first antenna 103 of the transceiver 101 that is provided at the high position of four corners of a room is an antenna having, for example, a directivity of about a half-value angle of 90 degrees, radio waves can be transferred to every corner of the room. When the transceiver 101 is provided in such a manner, the sensor modules 105 can be provided at any position in the room and high frequency power can be emitted to the sensor modules 105.

<Sensor Sheet 104>

The sensor sheet 104 is implemented by fixing a plurality of sensor modules 105 on a sheet 106. The sensor sheet 104 is provided in a range necessary for detecting a human body, for example, on a bed on which a human body lies. The sensor sheet 104 detects a position of the human body on the sheet 106, acquires state information about the human body, and transmits information of the position of the human body and state information to the transceiver 101.

FIG. 2 shows in detail the living body information identification system and the sensor modules according to the present embodiment. A view on a left side of FIG. 2 shows an example of the transceiver 101 and the sensor sheet 104, and a view on a right side shows in detail a portion surrounded by a dotted line in the left side view. The sensor sheet 104 includes a plurality of sensor modules 105 and the sheet 106 on which the sensor modules 105 are fixed.

<Sensor Module 105>

The sensor module 105 includes a second antenna 201, a power reception control unit 202, and a sensor 203. The sensor module 105 receives radio waves transmitted from the transceiver 101 via the second antenna 201, converts the received radio waves into power, and uses the power as a power supply to transmit held ID information to the transceiver 101.

The sensor module 105 is fixed on a predetermined position on the sheet 106. Specifically, the sensor modules 105 are separated from each other at a predetermined interval and fixed on the sheet 106 having, for example, a square shape. For example, the sensor modules 105 are separated at a predetermined interval and provided in five rows and five columns as shown in FIG. 2.

The sensor modules 105 may be provided in a state of contacting with each other without being separated from each other at an interval. Compared to a case where the sensor modules 105 are separated at a predetermined interval, a position of a human body can be accurately detected in a case where the sensor modules 105 are provided in a state of contacting with each other.

Information held by the sensor modules 105 includes position information of the sensor modules 105 on the sheet 106. For example, ID information held by the sensor module 105 in the third row and third column includes position information of a center sensor module 105 among the sensor modules 105 shown in the left side of FIG. 2.

The sheet 106 may have a function of electrically connecting the sensor modules 105. In this case, the sheet 106 includes a conductive member such as aluminum.

The second antenna 201 receives radio waves from the transceiver 101, and transmits information held by the sensor modules 105 to the transceiver 101. The second antenna 201 receives high frequency power emitted from the transceiver 101.

The sensor 203 detects a position of a human body within a range of the sensor modules 105 and acquires state information about a state of the human body.

The state information acquired by the sensor 203 includes various pieces of information such as information of a living body. The sensor 203 may include various sensors in accordance with information to be acquired. For example, in a case where acquired information is used for nursing care, it is necessary to acquire motion information in order to prevent a fall accident or the like. In such a case, it is preferable to use, for example, an acceleration sensor. When information to be acquired is about health, for example, a body temperature sensor or a heart rate sensor may be used. The sensor 203 is not limited to those described above and may include various sensors. The number of the sensor 203 is not limited to one, and a plurality of sensors 203 and a plurality of types of sensors 203 may be used in accordance with information to be acquired. For the convenience of description, one sensor 203 is described for one sensor module 105 in FIG. 2.

Figure 3:
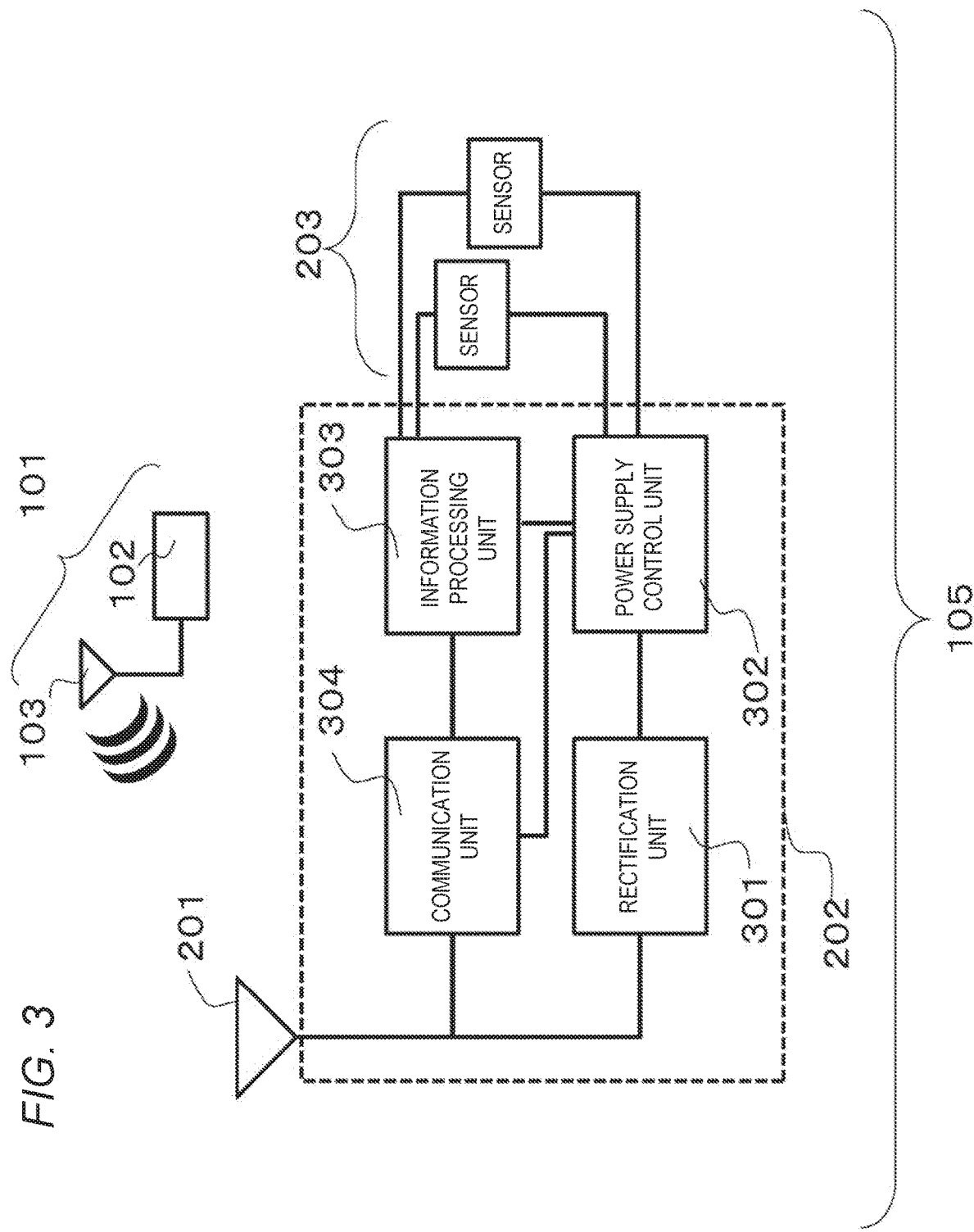
FIG. 3 shows a modification of a sensor module of the living body information identification system according to the embodiment.

FIG. 3 is a diagram showing a detailed structure of the sensor module 105 according to the present embodiment. The power reception control unit 202 includes a rectification unit 301, a power supply control unit 302, an information processing unit 303, and a communication unit 304.

The rectification unit 301 converts radio waves received from the transceiver 101 via the second antenna 201 into a direct current.

The power supply control unit 302 supplies the direct current generated by the rectification unit 301 to the sensor 203, the power supply control unit 302 and the information processing unit 303, and supplies power at a voltage at which the sensor 203, the power supply control unit 302 and the information processing unit 303 can be operated. The sensor 203 is connected to the power supply control unit 302 and the information processing unit 303.

The information processing unit 303 processes information acquired by the sensor 203 and has a function of transmitting the information to the transceiver 101 via the communication unit 304 at a certain timing.

The sensor modules 105 transmit ID information unique to the sensor modules 105 to the transceiver 101. Further, the sensor modules 105 transmit information acquired by the sensor 203 and receive an instruction from the transceiver 101.

By these functions, the sensor modules 105 can use the high frequency power emitted from the transceiver 101 as a power supply and wirelessly transmit the information acquired by the sensor 203 to the transceiver 101.

As shown in FIG. 3, a plurality of types of sensors can be connected to the power reception control unit 202. Alternatively, three or more sensors may be connected to the power reception control unit 202.

<Human Body Position Detection Operation>

Next, a method for detecting a position of a human body will be described. Specifically, when nobody is present on the sensor sheet 104, the transceiver 101 transmits radio waves and instructs the sensor modules 105 to transmit ID information. Then, the sensor modules 105 transmit the ID information to the transceiver 101. Thereafter, the transceiver 101 receives the ID information, and the oscillation control unit 102 associates each piece of the ID information with an intensity of the received radio waves and stores the intensity of the received radio waves into a memory provided in the oscillation control unit 102. The oscillation control unit 102 identifies positions of the sensor modules 105 based on the ID information received from the sensor modules 105, and determines an intensity of radio waves received at this time as a reference intensity.

After preparation is performed in such a manner in advance, an actual detection of a human body is performed as follows.

(1) The transceiver 101 transmits radio waves and instructs the sensor modules 105 to transmit ID information.

(2) The sensor modules 105 transmit the ID information to the transceiver 101.

(3) The transceiver 101 reads a reference intensity corresponding to the ID information received from the sensor modules 105 from the memory provided in the oscillation control unit 102, and compares the read reference intensity with an intensity of radio waves received from the sensor modules 105.

(4) Whether a human body is present in the vicinity of the sensor modules 105 is detected based on a change in the intensity of the received radio waves relative to the reference intensity.

As shown in FIG. 1, when a human body is present on the sensor modules 105, radio waves emitted from the sensor modules 105 are blocked by the human body. As a result, an intensity of radio waves received by the transceiver 101 is low. Whether a human body is present in the vicinity of the sensor modules 105 can be detected using this principle. The oscillation control unit 102 may set an amount of change relative to the reference intensity as a threshold in advance, and may determine that a human body is present on the sensor modules 105 when, for example, an intensity of received radio waves is lowered to 50% or less of the reference intensity. The threshold is not limited to 50% of the reference intensity, and may be, for example, 60% or 40% of the reference intensity. Even when the radio waves cannot be received and the ID information cannot be read, the oscillation control unit 102 may determine that an intensity of the radio waves is equal to or less than the threshold. According to this method, the sensor modules 105 on which the human body is present can be detected and identified among the plurality of the sensor modules 105. The radio waves from the sensor modules 105 can be easily blocked by a human body who lies on the sensor modules 105, and the human body can be easily detected. Therefore, it is preferable to provide the second antenna 201 to be directed to an upper side.

<Personal Identification Operation>

A method for identifying a detected human body is described.

(1) The transceiver 101 transmits an instruction to instruct the sensor modules 105 to transmit state information.

(2) The sensor modules 105 transmit personal ID information and state information acquired by the sensor modules 105 to the transceiver 101.

(3) The oscillation control unit 102 associates the ID information of the sensor modules 105 and the state information with an intensity of radio waves received from the sensor modules 105 and stores the ID information of the sensor modules 105, the state information, and the intensity of radio waves received from the sensor modules 105 into the memory provided in the oscillation control unit 102.

The transceiver 101 can identify a presence range in which the sensor modules 105 are present based on an estimated distance. The transceiver 101 can identify the sensor modules 105 on which a human body is present based on the intensity of radio waves received from the sensor modules 105. In addition, the transceiver 101 can estimate whether the human body lies or sits based on the number of or positions of the sensor modules 105 on which the human body is detected.

<When the Sensor Modules 105 Cannot Communicate with the Transceiver 101>

For example, when a person is present on the sensor modules 105 as shown in FIG. 1, the sensor modules 105 may not receive radio waves transmitted from the transceiver 101. Further, the transceiver 101 may not receive radio waves from the sensor modules 105. In such cases, it is preferable to electrically connect the sensor modules 105 on which the person is present with the sensor modules 105 on the sensor sheet 104. When the sensor modules 105 cannot receive radio waves from the transceiver 101, or when the sensor modules 105 cannot transmit radio waves to the transceiver 101, information or power can be transferred among the sensor modules 105 that are electrically connected on the sensor sheet 104. As a result, the transceiver 101 can acquire, via the other sensor modules 105 (a second sensor module), ID information or state information of the sensor modules 105 (a first sensor module) that cannot receive radio waves or cannot transmit radio waves to the transceiver 101.

Specifically, the transceiver 101 and the sensor modules 105 are operated as follows. (1) The transceiver 101 identifies the sensor modules 105 (the first sensor module) whose ID information is not read. The transceiver 101 determines that a person is present on the sensor modules 105 whose ID information is not read.

(2) The sensor modules 105 whose ID information is not read do not receive radio waves from the transceiver 101 and are not supplied with power converted from radio waves. Therefore, the transceiver 101 transmits, to the sensor modules 105 (the second sensor module) whose ID information is read, an instruction of transmitting power to the sensor modules 105 on which a person is present and that cannot receive radio waves.

(3) When the sensor modules 105 whose ID information is read receive radio waves from the transceiver 101, the sensor modules 105 whose ID information is read convert the received radio waves into power, and supply the power to the sensor modules 105 whose ID information is not read.

(4) The sensor modules 105 whose ID information is not read use the power supplied from the sensor modules 105 whose ID information is read to acquire state information of the human body on the sensor modules 105. The sensor modules 105 whose ID information is not read transmit the acquired state information and own ID information to the sensor modules 105 whose ID information is read.

(5) The sensor modules 105 whose ID information is read transmits the state information of the human body received from the sensor modules 105 whose ID information is not read and ID information of the sensor modules 105 whose ID information is not read to the transceiver 101.

In this manner, even when there are sensor modules 105 whose ID information is not read, the sensor modules 105 whose ID information is read can transmit ID information and the state information of the human body to the transceiver 101 in place of the sensor modules 105 whose ID information is not read.

<Effect>

ID information of the sensor modules 105 is used to detect a position of a human body. Therefore, detection of a position of a human body on the sensor sheet 104 can be implemented without the need to carry a special wireless device such as an ID reader.

In addition to detecting the position of the human body on the sensor sheet 104, the sensor modules 105 are provided with a sensor to detect information that needs to be acquired, so that various pieces of state information of a human body who lies on the sheet can be acquired without giving a feeling of pressure like in a case where a sensor is wrapped on a human body.

The living body information identification system according to the present disclosure can be widely used by providing the living body information identification system under a futon, a mattress of a bed, a seat surface of a chair, or the like.

What is claimed is:

1. A living body information identification system that identifies information of a living body, the living body information identification system comprising:
a transceiver configured to transmit a radio wave and wirelessly receive a signal; and
a plurality of sensor modules, each configured to receive the radio wave, convert the received radio wave into power, and use the power as a power supply to transmit own unique ID information to the transceiver, wherein
each of the sensor modules uses the power as a power supply to acquire state information about a state of the living body and transmit the state information to the transceiver,
the transceiver identifies a state of the living body based on the ID information and the state information,
the transceiver is positioned above the plurality of sensor modules,
the plurality of sensor modules are arranged on a sheet and are positioned below the living body,
the transceiver identifies whether or not the living body exists between the transceiver and the sensor modules based on a predetermined reference strength and a strength of radio waves received from the sensor modules,
the transceiver specifies at least one of the sensor modules on which the living body is detected, and
the transceiver estimates whether the living body is sitting or lying on the at least one of the sensor modules based on (i) a total number of the at least one of the sensor modules on which the living body is detected or (ii) positions of the at least one of the sensor modules on which the living body is detected.

2. The living body information identification system according to claim 1, wherein
the plurality of sensor modules are respectively provided in a predetermined range.

3. The living body information identification system according to claim 1, wherein
each of the plurality of sensor modules can receive and transfer information between each other.

4. The living body information identification system according to claim 3, wherein
the transceiver instructs a second sensor module of the plurality of sensor modules to transmit ID information of a first sensor module of the plurality of sensor modules or state information acquired by the first sensor module when the ID information or the state information cannot be received from the first sensor module.

5. The living body information identification system according to claim 1, wherein
each of the plurality of sensor modules can receive and transfer power between each other.

6. The living body information identification system according to claim 5, wherein
the transceiver instructs a second sensor module of the plurality of sensor modules to supply power to a first sensor module of the plurality of sensor modules when ID information and state information cannot be received from the first sensor module.

7. The living body information identification system according to claim 1, wherein
the state information includes information about motion information of the living body.

8. The living body information identification system according to claim 1, wherein
the state information includes information about health of the living body.

9. The living body information identification system according to claim 1, wherein
the ID information is position information of the respective sensor module.

10. A living body information identification method comprising:
a step of a transceiver transmitting a radio wave;
a step of sensor modules receiving the radio wave, converting the received radio wave into power, and using the power as a power supply to transmit own unique ID information to the transceiver;
a step of the sensor modules using the power as a power supply to acquire state information about a state of a living body and transmit the state information to the transceiver, the plurality of sensor modules being arranged on a sheet and positioned below the living body;
a step of the transceiver identifying a state of the living body based on the ID information and the state information, the transceiver being positioned above the plurality of sensor modules;
a step of the transceiver identifying whether or not the living body exists between the transceiver and the sensor modules based on a predetermined reference strength and a strength of radio waves received from the sensor modules;
a step of the transceiver specifying at least one of the sensor modules on which the living body is detected; and
a step of the transceiver estimating whether the living body is sitting or lying on the at least one of the sensor modules based on (i) a total number of the at least one of the sensor modules on which the living body is detected or (ii) positions of the at least one of the sensor modules on which the living body is detected.

11. The living body information identification system according to claim 1, wherein
the plurality of sensor modules are arranged on the sheet in a grid shape at predetermined intervals.

12. The living body information identification system according to claim 1, wherein
the plurality of sensor modules are arranged in contact with each other.

13. The living body information identification system according to claim 1, wherein
each of the sensor modules includes an antenna, a power reception control unit, and a sensor,
for each of the sensor modules,
the antenna receives radio waves from the transceiver, transmits information held by the sensor module to the transceiver, and receives high-frequency power radiated from the transceiver,
the sensor acquires information on the living body, and
the power reception control unit includes a rectifying unit, a power supply control unit, an information processing unit, and a communication unit,
wherein the rectifying unit converts a radio wave received via the antenna from the transceiver into a DC current, the power supply control unit supplies the DC current generated by the rectifying unit to the sensor, the power supply control unit, and the information processing unit at a voltage capable of operating the sensor, the power supply control unit, and the information processing unit, the power supply control unit and the information processing unit are connected to the sensor, the information processing unit processes the information acquired by the sensor, and transmits the processed information through the communication unit to the transceiver at a predetermined timing, and the antenna transmits ID information unique to each sensor module to the transceiver, transmits information of the sensor, and receives an instruction from the transceiver.

14. The living body information identification system according to claim 1, wherein each of the sensor modules comprises one or more of an acceleration sensor, a body temperature sensor, and a heart rate sensor.

15. A living body information identification system that identifies information of a living body, the living body information identification system comprising:

a transceiver configured to transmit a radio wave and wirelessly receive a signal; and a plurality of sensor modules, each configured to receive the radio wave, convert the received radio wave into power, and use the power as a power supply to transmit own unique ID information to the transceiver, wherein each of the sensor modules uses the power as a power supply to acquire state information about a state of the living body and transmit the state information to the transceiver, the transceiver identifies a state of the living body based on the ID information and the state information, the transceiver is positioned above the plurality of sensor modules, the plurality of sensor modules are arranged on a sheet and are positioned below the living body, the plurality of sensor modules are electrically connected to each other, the transceiver identifies whether or not the living body exists between the transceiver and the sensor modules based on a predetermined reference strength and a strength of radio waves received from the sensor modules, and when the human body is present on at least one of the sensor modules, and the at least one of the sensor modules is unable to receive radio waves transmitted from the transceiver, information and power are delivered between the plurality of electrically connected sensor modules.

16. The living body information identification system according to claim 1, wherein each of the sensor modules includes an antenna directed toward the transceiver.

17. The living body information identification system according to claim 1, wherein the transceiver includes an antenna having a directivity of approximately a half-value angle of 90 degrees or more.

* * * * *